(12) United States Patent
Germain et al.

(10) Patent No.: US 11,891,419 B2
(45) Date of Patent: Feb. 6, 2024

(54) WHEAT PROTEIN ISOLATES AND PROCESSES FOR PRODUCING

(71) Applicant: ARCHER DANIELS MIDLAND COMPANY, Decatur, IL (US)

(72) Inventors: Normand Germain, Vaudreuil-Dorian (CA); Michel Giroux, Repentigny (CA)

(73) Assignee: ARCHER DANIELS MIDLAND COMPANY, Decatur, IL (US)

(*) Notice: Subject to any disclaimer, the term of this patent is extended or adjusted under 35 U.S.C. 154(b) by 776 days.

(21) Appl. No.: 15/945,250

(22) Filed: Apr. 4, 2018

(65) Prior Publication Data
US 2018/0222948 A1  Aug. 9, 2018

Related U.S. Application Data

(63) Continuation of application No. 14/127,267, filed as application No. PCT/US2012/044109 on Jun. 26, 2012, now abandoned.

(60) Provisional application No. 61/501,306, filed on Jun. 27, 2011.

(51) Int. Cl.
| | |
|---|---|
| A23J 1/12 | (2006.01) |
| C07K 14/415 | (2006.01) |
| A23L 33/185 | (2016.01) |
| A23J 3/14 | (2006.01) |
| A61K 36/899 | (2006.01) |

(52) U.S. Cl.
CPC .............. *C07K 14/415* (2013.01); *A23J 1/12* (2013.01); *A23J 3/14* (2013.01); *A23L 33/185* (2016.08); *A61K 36/899* (2013.01)

(58) Field of Classification Search
CPC .................... A23J 1/12; A23J 3/18; A23J 3/12
See application file for complete search history.

(56) References Cited

U.S. PATENT DOCUMENTS

2005/0287267 A1* 12/2005 Maningat ................ A23J 3/227
426/549

FOREIGN PATENT DOCUMENTS

EP           0010447 A1 *  4/1980  ........... C08B 30/046

OTHER PUBLICATIONS

Adm, "Prolite Functional Wheat Proteins", https://assets.adm.com/Products-And-Services/Food-Ingredients/Milling/Wheat-Protein-Prolite-Sell-Sheet.pdf, downloaded Apr. 7, 2021. (Year: 2021).*

* cited by examiner

*Primary Examiner* — Elizabeth Gwartney
(74) *Attorney, Agent, or Firm* — Andrew F. Nilles

(57) ABSTRACT

Isolated wheat proteins that are substantially free of additives, processing aids, added acids, buffers, reagents, or added enzymes and compositions formed from the isolated wheat proteins are described. Methods of forming compositions which include isolated wheat proteins that are substantially free of additives, processing aids, added acids, buffers, reagents, or added enzymes are also described.

9 Claims, 3 Drawing Sheets

WHEAT PROTEIN ISOLATES AND PROCESSES FOR PRODUCING

CROSS REFERENCE TO RELATED APPLICATIONS

This application is a divisional of U.S. patent application Ser. No. 14/127,267, filed Dec. 19, 2013, which was a national state entry of International Application No. PCT/US2012/044109, filed Jun. 26, 2012, which itself claimed priority to U.S. Provisional Patent Application No. 61/501,306, filed Jun. 27, 2011, each of the contents of the entirety which is incorporated by this reference.

TECHNICAL FIELD

Various embodiments of the present disclosure relate to compositions comprising wheat proteins that are produced without the use of added acids or reducing agents, such as sulfites. Other embodiments relate to processes of isolating wheat proteins naturally, without any additives, processing aids, added acids, reagents, buffers, or added enzymes.

BACKGROUND

The development and production of wheat proteins isolates has continued. US Patent Application 2008/0254200 published about Oct. 16, 2008 describes the production of wheat protein isolates that are substantially free of sulfites. While the invention described in US Patent Application 2008/0254200 successfully produced a wheat protein isolate without using sulfites, such publication still used an added acid, such as lactic acid.

Wheat protein isolates are used in the food industry as an ingredient to alter texture and enhance taste and appearance in food products. Wheat protein isolates may add certain benefits to food products, including replacing sugar or carbohydrate functionalities in baked or processed foods; building structure or improving crumb texture in baked goods; improving freeze-thaw performance with improved texture and mouthfeel; replacing sugar as a binder in bars and coatings for cereals; increasing protein levels in foods without sacrifice of taste and texture; improving dough rheology, proofing times, and sheeting performance; reducing fat in food products; generating foam and other types of controlled air entrapment; and improving taste and texture in whole grain applications.

While US Patent Application 2008/0254200 successfully produced a wheat protein isolate without a reducing agent, a need exists for the production of wheat protein isolates that do not have any additives, processing aids, added acids, buffers, reagents, or added enzymes and that have a clean ingredient label.

SUMMARY OF THE INVENTION

In each of its various embodiments, the present invention fulfills these needs and discloses methods for producing wheat proteins without additives, processing aids, added acids, buffers, reagents, or added enzymes. In another embodiment, the present invention is directed towards a naturally produced wheat protein isolate that has unique properties such as rheology, water adsorption, taste, film forming, and binding.

In one embodiment, a composition comprises an isolated wheat protein. The composition is substantially free of additives, processing aids, reagents, added acids, buffers, and added enzymes, and has less than 10% moisture by weight.

In another embodiment, a process for producing an isolated wheat protein comprises mixing water and wheat gluten to form a gluten slurry and agitating the gluten slurry at a temperature between 15° C. and 55° C. for a time sufficient to produce an isolated wheat protein. An acid and buffer are not added to the gluten slurry during the process.

DETAILED DESCRIPTION OF THE INVENTION

Figure 1:
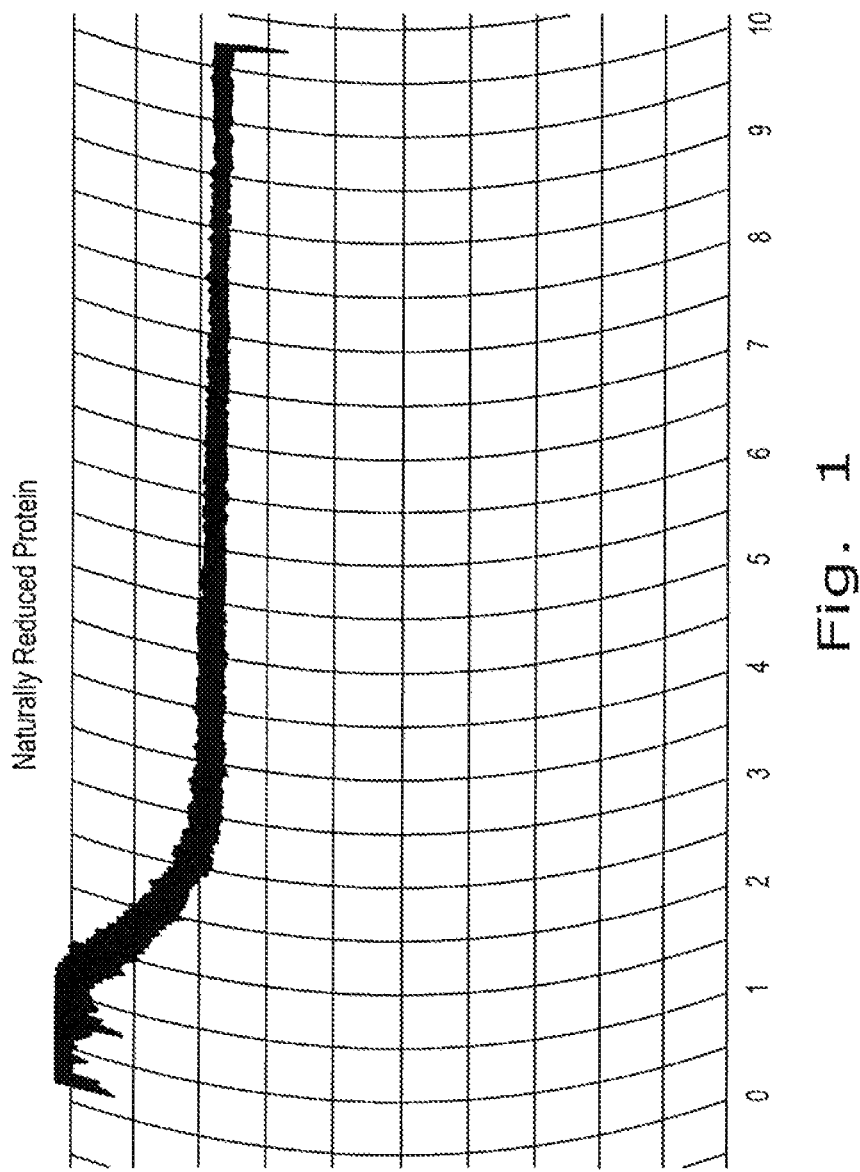
FIG. 1 shows a mixograph of one embodiment of a wheat protein isolate produced according to the present invention.

Various embodiments of the present disclosure relate to processes for producing isolated wheat proteins and the compositions produced therefrom. The wheat protein isolates of the present invention are natural in that they don't have additives, processing aids, added acids, buffers, reagents, or added enzymes and have a clean ingredient label.

Other than the operating examples or where otherwise indicated, all numbers expressing quantities of ingredients, processing conditions, and the like used in the specification and claims are to be understood as being modified in all instances by the term "about". Unless indicated to the contrary, the numerical parameters set forth in the following specification and claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Any numerical values disclosed herein may inherently contain certain errors, such as, equipment and/or operator error, necessarily resulting from the standard deviation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of less than or equal to 10.

Any patent, publication, or other disclosure material, in whole or in part, that is said to be incorporated by reference herein is incorporated herein only to the extent that the incorporated material does not conflict with existing definitions, statements, or other disclosure material set forth herein. As such, and to the extent necessary, the disclosure set forth herein supersedes any conflicting material incorporated by reference. Any material, or portion thereof, that is said to be incorporated by reference, but which conflicts with existing definitions, statements, or other disclosure material set forth herein will only be incorporated to the extent that no conflict arises between that incorporated material and the existing disclosure material.

The present disclosure describes several different features and aspects of the various exemplary embodiments. It is understood, however, that the present disclosure embraces numerous alternative embodiments, which may be accomplished by combining any of the different features, aspects, and embodiments described herein in any combination that one of ordinary skill in the art would find useful.

According to certain embodiments, the present disclosure provides for a composition comprising an isolated wheat protein that is produced naturally in that it does not include additives, processing aids, added acids, buffers, reagents, or added enzymes. In one embodiment, the isolated wheat protein may comprise at least 60% protein by weight, as determined by measuring nitrogen content and multiplying by 5.7. In another embodiment, the protein content may be determined by measuring nitrogen content and multiplying by 6.25. As used herein, the term "substantially free" when used in reference to additive, processing aid, added acid, buffer, reagent, or added enzyme concentrations, includes the additive, the processing aid, the added acid, buffer, the reagent, or the added enzyme concentration that is below the measurable limit using standard analytical procedures. According to certain embodiments, the isolated wheat protein may have an additive, processing aid, added acid, buffer, reagent, or added enzyme concentration of less than 0.001% by weight (i.e., less than 10 ppm). According to other embodiments, the isolated wheat protein may have an additive, processing aid, added acid, buffer, reagent, or added enzyme concentration of 0% by weight.

There has been a growing desire for products and food compositions that are all natural and/or organic (as defined by various regulating agencies). Certain regulatory agencies may limit or regulate how compositions containing additives, processing aids, added acids, buffers, reagents, or added enzymes may be described. For example, in certain markets, the presence of additives, processing aids, added acids, buffers, reagents, or added enzymes in a product or food composition may preclude the use of certain monikers, descriptors, or indicia. For example, in certain markets, the presence of additives, processing aids, added acids, buffers, reagents, or added enzymes in a product or food composition may prevent the use of descriptors, such as, for example, "organic" or "natural" when describing the product or food composition. Thus, modified wheat proteins that are produced by recognized commercial processes may not be described as "natural" or "organic" due to these restrictions. However, the compositions of the present disclosure comprising isolated wheat proteins that are substantially free of additives, processing aids, added acids, buffers, reagents, or added enzymes will not be subject to these regulations.

The isolated wheat proteins of the present disclosure may have improved properties and characteristics compared to wheat protein isolates that are not produced naturally. For example, the isolated wheat proteins of various embodiments described herein may have improved properties such as rheology, water absorption, taste, film forming, or binding.

As described herein, the isolated wheat proteins of the present disclosure may be produced from wheat gluten, vital wheat gluten, wheat protein isolates, or wheat protein concentrates. Wheat protein isolates may have a protein content of at least 75% by weight, whereas wheat protein concentrates may have a protein content of at least 60% by weight. Thus, the isolated wheat proteins of the present disclosure may have a protein content of at least 60% by weight.

According to other embodiments, the isolated wheat proteins of the present disclosure may have a protein content of at least 75% by weight. According to still other embodiments, the isolated wheat proteins of the present disclosure may have a protein content of at least 80% by weight. In certain embodiments, the isolated wheat proteins of the present disclosure may have a maximum protein content of 99% by weight. The protein content of the isolated wheat proteins of the present disclosure may be measured by any method known in the art. For example, one method of measuring the protein content in a food composition is the Kjeldahl method which involves measuring the nitrogen content in the modified wheat protein isolates (for example by a chemical degradation) and multiplying by 5.7 (corresponding to the nitrogen content of wheat proteins). In other embodiments, the protein content may be calculated by multiplying the nitrogen content by 6.25. Other methods for measuring the nitrogen content in the isolated wheat proteins, such as combustion nitrogen analysis (the "Dumas method"), may also be used.

The present disclosure also provides for food compositions that comprise the isolated wheat proteins that are substantially free of additives, processing aids, added acids, buffers, reagents, or added enzymes according to any the various embodiments disclosed herein. Food compositions may include, but are not limited to, baked goods, processed foods, whole grain foods, food bars, cereals, granolas, doughs and batters, cakes, tortillas, snacks, cookies, microwave bakery products, whips, fillings, frostings, frozen foods, wieners, sausages, meat loaf, meat patties, dressings, spreads, pet foods, fish feeds, shrimp feed, or animal feeds.

According to other embodiments, the present disclosure provides processes for producing an isolated wheat protein that are substantially free of additives, processing aids, added acids, buffers, reagents, or added enzymes. According to one embodiment, the process for producing an isolated wheat protein may comprise mixing water and wheat gluten to form a gluten slurry, agitating the gluten slurry at a reaction temperature for a time sufficient to produce an isolated wheat protein, wherein the isolated wheat protein is substantially free of additives, processing aids, added acids, buffers, reagents, or added enzymes. According to certain embodiments, the isolated wheat protein may have an additive, processing aid, added acid, buffer, reagent, or added enzyme concentration of less than 0.001% by weight (less than 10 ppm). According to other embodiments, the isolated wheat protein may have an additive, processing aid, added acid, buffer, reagent, or added enzyme concentration of 0% by weight. In another embodiment, a pH of the gluten slurry after adding the gluten to the water is above pH 4.5.

In certain embodiments, the reaction temperature may range from 15° C. to 52° C. In other embodiments, the temperature may range from 34° C. to 45° C. In other embodiments, the temperature may range from 43° C. to 47° C.

The gluten slurry may be formed by mixing water and wheat gluten, such as a wet wheat gluten, to form the slurry. In certain embodiments, the mixing may be performed at the reaction temperature or a temperature higher than the reaction temperature (such as the water temperature). The wheat gluten may be added to the water in such an amount to result in a gluten slurry having a total solids content ranging from 6% to 22% on a dry basis. In another embodiment, the gluten slurry may have a total solids content ranging from 11% to 18% on a dry basis. In another embodiment, the gluten slurry may have a total solids content ranging from 14% to 16.5% on a dry basis.

The gluten slurry may be agitated at the reaction temperature for a time sufficient to produce an the gluten slurry having a desired viscosity. For example, according to certain embodiments, the gluten slurry may have a Brookfield viscosity (as defined herein) ranging from 170 cps to 360 cps. As used herein, "agitation" and "agitating" include stirring the gluten slurry, mixing the gluten slurry, mixing the gluten slurry with a high shear (e.g., using a high shear mixer), agitating the gluten slurry, and sonicating the gluten slurry or any combinations of these agitation methods. In certain embodiments, agitating the gluten slurry is performed using a high shear, such as, for example, mixing at a high speed. In other embodiments, agitating the gluten slurry is performed using a standard mixing speed. As the gluten slurry is agitated over the reaction time, the viscosity of the slurry will decrease. In various embodiments, as the gluten slurry viscosity decreases, the mixing speed may also be decreased. For example, in one embodiment, after the viscosity of the gluten slurry has decreased to approximately 200 cps to 220 cps, the speed of the agitator may be lowered, for example from a high speed to a medium or low speed.

In other embodiments, the gluten slurry may be agitated for a time sufficient to produce an isolated wheat protein having a Brookfield viscosity ranging from 17 cps to 390 cps at room temperature. In certain embodiments, the gluten slurry may be agitated, for example, at a high speed, for a time period ranging from 175 minutes to 380 minutes. In another embodiment, the time period may range from 190 minutes to 230 minutes. In other embodiments, wherein a lower or more vigorous agitation is used, it will be understood that the agitation time will be adjusted accordingly. For example, in certain embodiments, where a lower energy agitation is used, the agitation time may be increased, whereas in embodiments where a higher energy agitation is used, the agitation time may be shortened.

After agitating the gluten slurry to form the isolated wheat protein, the isolated wheat protein product may be separated from any residual bran remaining in the reactor. For example, the isolated wheat protein product may be separated from the residual bran, or may be removed from the residual bran by other means known in the art.

In certain embodiments, the isolated wheat protein product from the agitation, such as the aqueous slurry of the isolated wheat protein, may be held in a holding tank prior to drying. In certain embodiments, the holding tank may be equipped with a variable speed agitator, such as an agitator with a speed variable between 30 rpm and 500 rpm. Agitation of the slurry may aid in maintaining the isolated wheat protein in a soluble "liquid" form, such as a liquid having a viscosity ranging from 20 cps to 1000 cps, and in another embodiment from 40 cps to 300 cps. In certain embodiments, agitation of the isolated wheat protein product in the holding tank may prevent the slurry from thickening, for example to a higher viscosity, while in the holding tank or may prevent formation of a film on the surface of the slurry. Maintaining the viscosity of the slurry at acceptable levels may also assist in transporting the slurry from one site to another, for example, when pumping the slurry from the holding tank to the dryer, such as via a transfer pipe or other transfer mechanism used in the art.

Certain embodiments of the processes of the present disclosure may further comprise drying the isolated wheat protein, for example, to remove water from the product. For example, the slurry comprising the isolated wheat protein that is substantially free of additives, processing aids, added acids, buffers, reagents, or added enzymes, may be dried at an air temperature ranging from 320° F. to 500° F. The isolated wheat protein may be dried for a time sufficient to provide an isolated wheat protein product having a product temperature ranging from 160° F. to 230° F. In certain embodiments, the isolated wheat protein may be dried to a moisture content ranging from 0.1% to 10.0% moisture by weight. In other embodiments, the isolated wheat protein may be dried to a moisture content ranging from 0.1% to 7.0%; in still other embodiments, a moisture content ranging from 4.0% to 6.0%; and in still other embodiments, a moisture content of 5.0%. In still other embodiments, the moisture content may be less than 7% by weight. In various embodiments, the internal temperature of the dryer may be increased, wherein the higher temperature may damage the gluten structure, thereby reducing its functionality (as shown by a lower line in a mixograph). The dried isolated wheat protein product may be cooled to room temperature. The isolated wheat protein may be dried by any means recognized in the art. For example, in one embodiment the isolated wheat protein may be dried in a drying oven at a temperature from 320° F. to 500° F. The drying oven may be at ambient pressure or, in certain embodiments, the drying oven may be at reduced pressure. In other embodiments, the isolated wheat protein may be dried by freeze drying, spray drying, ring drying, or flash drying. Various combinations of any of these drying methods are also contemplated.

In various embodiments, the dried isolated wheat protein of the present invention may have a powder, granular, or particulate formulation. For example, according to one embodiment, the dried isolated wheat protein may be granular in form, having a size such that at least 85% of the isolated wheat protein grains are able to pass through a #60 mesh USBS sieve. That is, a #60 mesh sieve has sieve openings of 250 μm and therefore, at least 85% of the isolated wheat protein grains will have a size less than 250 μm. In other embodiments, the dried isolated wheat protein may have a granular form having a size such that at least 95% of the isolated wheat protein grains are able to pass through a #60 mesh USBS sieve.

In one embodiment, the wheat protein isolate of the present invention may have a solubility of between 62 and 99 in water. In another embodiment, the wheat protein isolate may have a mixograph of between 3 and 10.

In other embodiments of the process for producing the isolated wheat protein of the present invention, the isolated wheat protein may have improved characteristics as compared to a modified wheat protein isolate that is not substantially free of additives, processing aids, added acids, buffers, reagents, or added enzymes.

Improved foaming characteristics may include, for example, improved (i.e., greater) stiffness of foams, improved longevity or stability of the foam, and/or faster foaming time as compared to a modified wheat protein isolate that is not substantially free of additives, processing aids, added acids, buffers, reagents, or added enzymes. For example, certain embodiments of the isolated wheat protein of the present disclosure may achieve a full foam in less time than it takes a modified wheat protein isolate that is not substantially free of additives, processing aids, added acids, buffers, reagents, or added enzymes to achieve a full foam. In other embodiments, the isolated wheat protein produced by the processes of the present disclosure may have a more desirable flavor profile, such as, a blander flavor, than modified wheat protein isolates that are not substantially free of additives, processing aids, added acids, buffers, reagents, or added enzymes.

In other embodiments, the processes of the present disclosure may further comprise placing the isolated wheat protein into a container, such as a container that is configured for shipping. In still other embodiments, the processes may further comprise associating indicia with the container, wherein the indicia are capable of informing a user or consumer of the content of the container. Still other embodiments may further comprise shipping the container, for example by means of an airplane, ship, truck, railcar, or combinations of any of these shipping methods. The container may be shipped, for example, from a first geographic location to a second geographic location.

Further embodiments of the present disclosure provide a process for producing a food composition. The process may comprise incorporating an isolated wheat protein of the present invention into the food composition. Food compositions may include, but are not limited to, baked goods, processed foods, whole grain foods, food bars, cereals, granolas, doughs and batters, cakes, tortillas, snacks, cookies, microwave bakery products, frozen foods, wieners, sausages, meat loaf, meat patties, whips, fillings, frostings, dressings, spreads, pet foods, fish feeds, shrimp feed, or animal feeds.

Other embodiments of the present disclosure provide a composition comprising an isolated wheat protein that may be free of additives, processing aids, added acids, buffers, reagents, or added enzymes. Still other embodiments include a composition consisting essentially of an isolated wheat protein produced naturally, that is, without additives, processing aids, added acids, buffers, reagents, or added enzymes. Still other embodiments include a composition consisting of an isolated wheat protein produced naturally, that is, without additives, processing aids, added acids, buffers, reagents, or added enzymes.

Without intending to be limited by theory, it is thought that the naturally produced wheat protein isolate of the present invention may be achieved by the natural production of organic acids during the reaction process. For instance, at the time and temperature of the reaction conditions, it is thought that microbes in the reaction vessel may produce natural, organic acids and/or other chemicals during growth of the microbes and that such organic acids and/or other chemicals may aid in the production of the natural wheat protein isolate of the present invention.

In other embodiments, the isolated wheat protein product may have a pH from 3.0 to 5.0. In certain embodiments, the pH of the isolated wheat protein product may range from 3.9 to 4.9. The pH of the isolated wheat protein may be adjusted to the desired pH level by the addition of one or more basic or alkali ingredient or reagent, such as, for example, phosphate salts, soda ash, sodium bicarbonate, and other alkali reagents. Other embodiments of the compositions may further comprise a phosphate, such as a phosphate salt or phosphoric acid. One example of a phosphate salt that may be used includes, but is not limited to, sodium phosphate. In one embodiment, the amount of phosphate that may be used is a range of from 0.25-5% on a dry basis in the powder composition. Adjusting the pH of the isolated wheat protein product may result in an isolated wheat protein having one or more of good film forming properties, good elastic properties, higher viscosity, or other properties.

EXAMPLES

The following exemplary, non-limiting examples are provided to further describe the embodiments presented herein. Those having ordinary skill in the art will appreciate that variations of these Examples are possible within the scope of the invention.

Example 1

Wheat gluten was mixed with water to form a slurry for runs 1-13 at the solids percent (%) of Table 1. The slurry was mixed at the temperatures of Table 1 for each run for the amount of reaction time needed to reach about 200 cps or between 170-240 cps, and the slurry was cut (under high shear mixing) every 15 minutes. The mixing was performed with an overhead mixer for two hours to increase solubility. Throughout the reaction, pH, solubility, and viscosity were recorded. After the reaction, the slurry was over dried overnight and the dried product was ground. Tests were done to determine solubility, pH, and mixograph on the final, ground product and the results are shown in Table 1. A graph of the mixograph is shown in FIG. 1, which shows a smooth line indicative of a wheat protein isolate.

TABLE 1

Conditions used to produce the natural wheat protein isolate and properties of natural wheat proteins produced according to Example 1.

| Run | Temperature, °C. | Solids % | Reaction time, Achieve 200 cp | Solubility | pH | Mixograph |
|---|---|---|---|---|---|---|
| 1 | 36.0 | 15.50 | 380 | 67.2 | 4.00 | 9.2 |
| 2 | 34.6 | 13.75 | 380 | 64.2 | 4.04 | 9.7 |
| 3 | 39.5 | 13.75 | 245 | 66.7 | 4.05 | 9.8 |
| 4 | 44.4 | 13.75 | 200 | 74.3 | 3.96 | 7.9 |
| 5 | 39.5 | 13.75 | 225 | 65.2 | 4.10 | 8.3 |
| 6 | 43.0 | 15.50 | 210 | 68.9 | 4.04 | 7.7 |
| 7 | 39.5 | 13.75 | 225 | 68.3 | 4.10 | 8.7 |
| 8 | 36.0 | 12.00 | 290 | 62.1 | 4.12 | 9.8 |
| 9 | 39.5 | 11.28 | 190 | 62.5 | 4.10 | 10 |
| 10 | 39.5 | 13.75 | 210 | 66.2 | 4.05 | 10 |
| 11 | 43.0 | 12.00 | 175 | 68.9 | 4.08 | 9.2 |
| 12 | 39.5 | 16.22 | 290 | 67.8 | 4.13 | 9.6 |
| 13 | 39.5 | 13.75 | 220 | 66.6 | 4.05 | 9.5 |

Example 2

Figure 2:
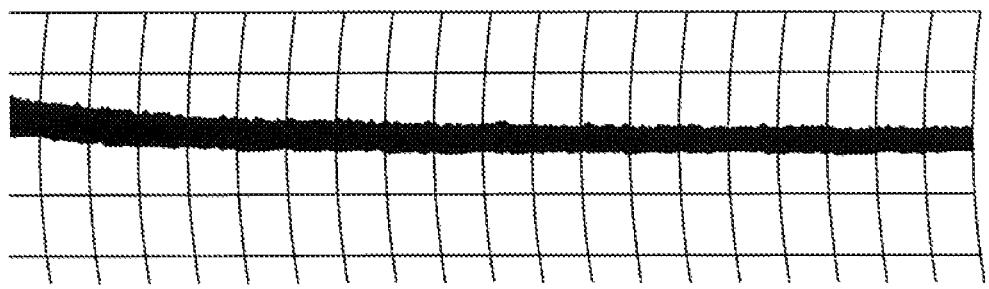
FIG. 2 shows a mixograph of one embodiment of a wheat protein isolate produced according to the present invention.

6000 pounds of 30% solids wheat gluten was mixed with 520 gallons of water to form a slurry. The slurry was mixed at about 48.3° C. reaction temperature for a 90 minute reaction time until the slurry reached about 380 cps, at which point the slurry had a pH of about 4.2. The slurry was spray dried to form the wheat protein isolate. A mixograph of the wheat protein isolate produced in this example is shown in FIG. 2.

The wheat protein isolate of this example has a moisture content of about 4.5%; a protein of at least 90% (measured by nitrogen content times 6.25); a pH of about 4.4; a mixograph of about 5.0; and a gravity solubility of about 97%.

Example 3

520 gallons of water having a temperature of 122° F. and a pH of 6.6 was placed in a tank. 6000 pounds of 32.9% solids wheat gluten having a pH of 5.8 was added to the water and mixed with an agitator, thus forming a slurry. After about 25 minutes of mixing after the wheat gluten was added, the slurry had a pH of 4.9 and a temperature of 114° F. After about 45 minutes of mixing after the gluten was added, the slurry had a pH of 4.3, a temperature of 113° F., a % refractometer reading of 17.8%, and a Brookfield viscosity of 900 cps. After about 80 minutes of mixing after the gluten was added, the slurry has a pH of 4.2, a % refractometer reading of 17.8%, and a Brookfield viscosity of 380 cps. At this time, the rate of mixing or agitation was slowed. After about 85 minutes (i.e., a reaction time of 85 minutes) of mixing after the gluten was added, the slurry had a pH of 4.2, a % refractometer reading of 17.8%, and a Brookfield viscosity of 270 cps and the reaction was stopped.

Figure 3:
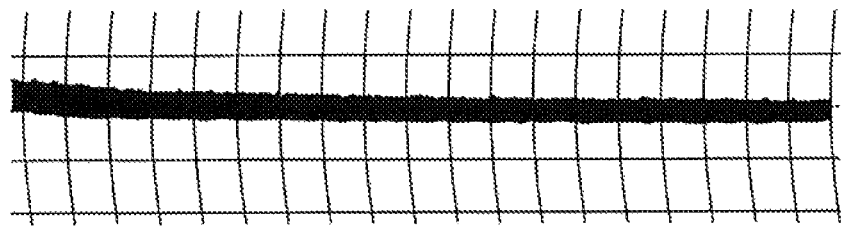
FIG. 3 shows a mixograph of one embodiment of a wheat protein isolate produced according to the present invention.
Figure 4:
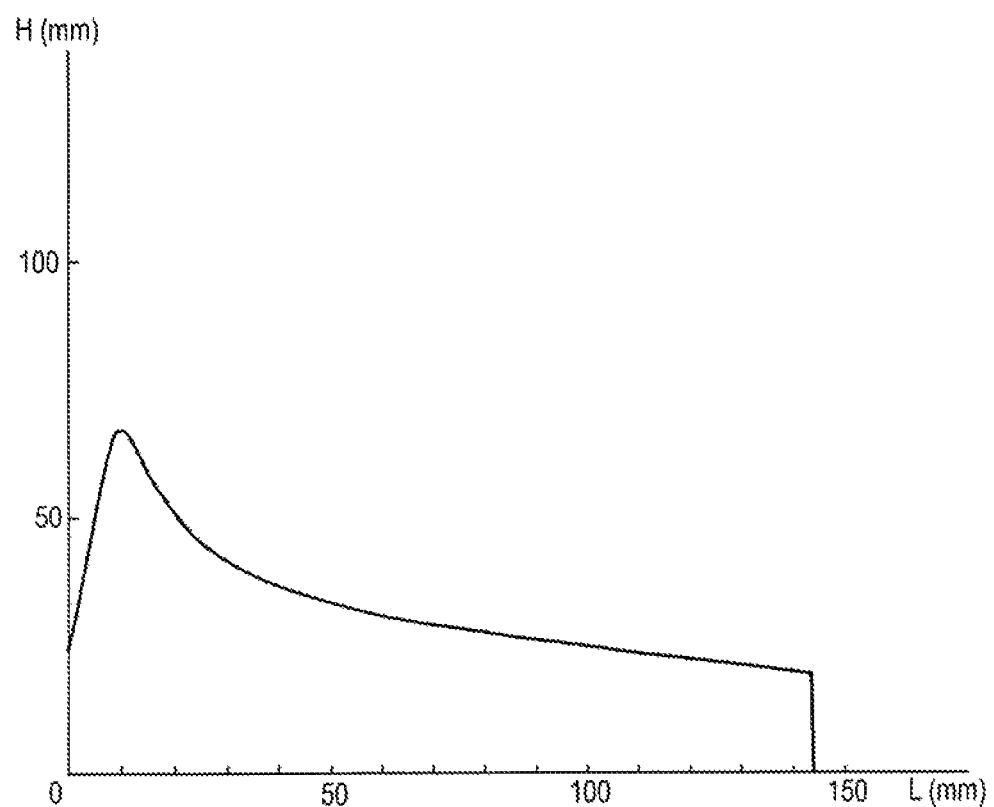
FIG. 4 is an alveograph of an embodiment of a wheat protein isolate produced according to the present invention.

The slurry was sent to the decanter and spray dried. The final product has the following characteristics: 93.8% protein (N×6.25) on a dry basis; a % solubility of 99.4% in a 10% solution in water; an excellent foam test; and a mixograph of 6. A mixograph of the wheat protein isolate produced in this example is shown in FIG. 3. An alveograph of the wheat protein isolate produced in this example is shown in FIG. 4.

This disclosure has been described with reference to certain exemplary embodiments, compositions and uses thereof. However, it will be recognized by those of ordinary skill in the art that various substitutions, modifications, or combinations of any of the exemplary embodiments may be made without departing from the spirit and scope of the disclosure. Thus, the disclosure is not limited by the description of the exemplary embodiments, but rather by the claims as originally filed.

What is claimed is:

1. A process for producing an isolated wheat protein, comprising:
    mixing water and a composition comprising wheat protein, the composition having a protein content of at least 60% by weight to form a slurry;
    determining a viscosity of the slurry;
    agitating the slurry at a temperature between 15° C. and 52° C. until a viscosity of the slurry reaches between 170-240 cps, thus producing an isolated wheat protein;
    drying the isolated wheat protein;
    wherein at least 85% of granules of the dried isolated wheat protein are unable to pass through a #60 mesh sieve;
    wherein neither an acid or a buffer are added to the slurry during the process; and
    wherein the composition comprising the wheat protein is selected from the group consisting of wheat gluten, vital wheat gluten, wheat protein isolates, or wheat protein concentrates.

2. The process of claim 1, wherein the slurry has an additive, processing aid, reagent, added acid, buffer, and added enzyme concentration of less than 0.001% by weight.

3. The process of claim 1, wherein the time ranges from 30 to 380 minutes.

4. The process of claim 1, wherein the slurry has a total solids content ranging from 6% to 22% on a dry basis.

5. The process of claim 1, wherein a pH of the slurry after adding the wheat gluten to the water is above 4.5.

6. The process of claim 1, wherein a pH of the slurry after the time sufficient to produce the isolated wheat protein is 3.0-5.0.

7. The process of claim 1, wherein drying the isolated wheat protein comprises spray drying.

8. A product produced by the process of claim 1.

9. A process for producing an isolated wheat protein, comprising:
    mixing water and a composition comprising wheat protein, the composition having a protein content of at least 60% by weight to form a slurry having a total solids content ranging from 6% to 22% on a dry basis and a pH of above 4.5;
    determining a viscosity of the slurry;
    agitating the slurry at a temperature between 15° C. and 52° C. for a time of from 30 to 380 minutes and to a viscosity of between 170-240 cps, thus producing an isolated wheat protein;
    drying the isolated wheat protein;
    wherein at least 85% of granules of the dried isolated wheat protein are able to pass through a #60 mesh sieve; where in neither an acid or a buffer are added to the slurry during the process; and
    wherein the composition comprising the wheat protein is selected from the group consisting of wheat gluten, vital wheat gluten, wheat protein isolates, or wheat protein concentrates.

* * * * *